United States Patent [19]

Uvarov et al.

[11] 4,246,134
[45] Jan. 20, 1981

[54] CATALYST FOR DI-, OLIGO-, CO- AND POLY- MERIZATION OF VINYL MONOMERS

[76] Inventors: Boris A. Uvarov, Ryazansky prospekt, 31, kv. 22; Valentina I. Tsvetkova, Leninsky prospekt, 3, kv. 23; Fridrikh S. Dyachkovsky, Vorobievskoe shosse, 2-b, kv. 9; Oleg M. Zvyagin, Kapotnya, III kvartal, 10, kv. 10, all of Moscow; Vladimir P. Konovalov, ulitsa Komsomolskaya, 15, kv. 62, Ljubertsy Moskovskoi oblasti; Elvira A. Uvarova, Ryazansky prospekt, 31, kv. 22, Moscow; Elena I. Ljustgarten, pereulok A. Gaidara, 7, kv. 6, Moscow; Ljudmila A. Novokshonova, ulitsa 26 Bakinskikh Komissarov 7, korpus 4, kv. 38, Moscow; Olga I. Kudinova, ulitsa Malakhovskaya, 15, Kratovo Moskovskoi oblasti; Tatyana A. Maklakova, Leningradskoe shosse, 8/2, kv. 57, Moscow, all of U.S.S.R.

[21] Appl. No.: 963,842

[22] Filed: Nov. 27, 1978

[51] Int. Cl.$^3$ .............................................. C08F 4/02
[52] U.S. Cl. .............................. 252/429 B; 526/141; 526/142; 526/159

[58] Field of Search .................................. 252/429 B

[56] References Cited

U.S. PATENT DOCUMENTS

| | | |
|---|---|---|
| 3,600,367 | 8/1971 | Delbouille et al. .......... 252/429 B X |
| 3,642,748 | 2/1972 | Iwasaki et al. ............... 252/429 B X |
| 3,769,233 | 10/1973 | Hermans et al. ............ 252/429 B X |
| 4,098,979 | 7/1978 | Maemoto et al. ........... 252/429 B X |

*Primary Examiner*—Patrick Garvin
*Attorney, Agent, or Firm*—Lackenbach, Lilling & Siegel

[57] ABSTRACT

A catalyst according to the present invention for di-, oligo-, co- and poly- merization of vinyl monomers consists of an active phase comprising a compound of a transition metal of Groups IV–V of the periodic system deposited onto a polymeric carrier, viz, a macroporous copolymer of vinyl and divinyl monomers with a specific surface area of 30 to 700 m$^2$/g and a co-catalyst such as an organo-aluminum compound. The catalyst according to the present invention makes it possible to obtain dimers in high yields of more than 6,000 kg as calculated for 1 g of the transition metal for 2 hours and polymers in yields of up to 72 kg per 1 g of the transition metal. The catalyst according to the present invention makes it possible to control the particle size of the resulting (co) polymer which enables the use of the (co) polymer avoiding the stage of granulation.

12 Claims, No Drawings

4,246,134

CATALYST FOR DI-, OLIGO-, CO- AND POLY-MERIZATION OF VINYL MONOMERS

FIELD OF THE INVENTION

The present invention relates to polymers and, more particularly, to a catalyst for di-, oligo-, co- and polymerization of vinyl monomers which is useful in the production of polymers.

BACKGROUND OF THE INVENTION

Known in the art are catalysts for dimerization, oligomerization, co- and poly-merization of ethylene and α-olefins which consist of an active phase, i.e. a transition metal compound deposited onto the surface of inorganic or organic carriers and various organo-metallic compounds.

The use of catalysts containing inorganic carriers results in an increased ash content of the polymer and, in some cases, impaired physico-mechanical properties thereof. Thus, the use of magnesium chloride (cf. U.S. Pat. No. 3,243,422; FRG (German) Pat. No. 2,033,468) as the inorganic carrier substantially impairs the dielectric constant of the resulting polymer and causes corrosion of the equipment during processing thereof.

The use of catalysts containing organic carriers is less effective due to a small specific surface area and a small total volume of pores of the carriers employed. Such catalysts possess a low specific activity (cf. French Pat. No. 1,550,186).

Also known in the art is a catalyst for polymerization of ethylene and propylene consisting of a compound of a transition metal of Groups IV–VI and VIII of the periodic system deposited onto polyolefines with a particle size of from 0.25 to 0.5 mm and a co-catalyst, viz. an organo-metallic compound (cf. FRG application No. 1,943,751).

The use of a large-size fraction of a polyolefin such as polyethylene for the catalyst preparation makes it possible to obtain large-size particles of a polymer without, however, providing for a possibility of control of the granulometric composition of the polymer obtained in the synthesis.

Other disadvantages of said catalyst reside in its rather low specific activity, a small yeld and a high ash-content of the resulting polymer.

SUMMARY OF THE INVENTION

One of the main objects of the present invention is to increase specific activity of the catalyst.

Another object of the present invention is to ensure the possibility of controlling the granulometric composition of the resulting (co)polymer.

Still another object of the present invention is to lower the ash-content of the resulting (co)polymer without washing thereof.

These objects are accomplished by the provision of a catalyst for di-, oligo-, co-, and poly-merization of vinyl monomers which consists of an active phase, viz. a compound of a transition metal of Groups IV–V of the periodic system deposited onto a polymeric carrier comprising a macroporous copolymer of vinyl and divinyl monomers with a specific surface area of from 30 to 700 m$^2$/g and a co-catalyst, viz. an organo-aluminum compound.

The term "macroporous copolymer" as used hereinafter means a two-phase system, wherein the polymeric compound is pierced with communicating cavities (pores) capable of being filled with an external medium upon submersion thereinto.

The use, in said catalyst, of said carrier with a specific surface area of below 30 m$^2$/g is inexpedient due to a low activity of the catalyst. The use, in said catalyst, of said carrier with a specific surface area of above 700 m$^2$/g is hindered due to technological difficulties of production of such a carrier. It is preferable that the catalyst contain a carrier with a pore volume within the range of from 0.3 to 2.8 cm$^3$/g.

The use of a carrier with a pore volume of below 0.3 cm$^3$/g is inefficient, since the carrier would have a small capacity with respect to the active phase, whereas above 2.8 cm$^3$/g pore volume of the carrier use of the latter is hindered due to a high brittleness of such a carrier.

It is preferable that the catalyst contain, as the carrier, a copolymer of styrene and divinylbenzene, a copolymer of styrene and diisopropenylbenzene, a copolymer of styrene, divinylbenzene and methylmethacrylate, or a copolymer of styrene, ethyldivinylbenzene and vinylpyridine.

The use, as the carrier, of one of the above-mentioned copolymers of vinyl and divinyl monomers makes it possible to substantially increase the specific activity of the catalyst.

It is preferable that the catalyst have a particle size within the range of from 0.001 to 1 mm.

The use of a catalyst with the particle size of from 0.001 to 1 mm makes it possible to control the particle size and distribution with respect to the size of the resulting polymer particles.

It is preferable to have the catalyst in a granulated form.

The control of the shape of the catalyst particles makes it possible to obtain, during the synthesis, polymeric particles of such a shape which ensures the most favorable hydrodynamic conditions in the reactor.

The catalyst should preferably contain, as the active phase, a compound of titanium or vanadium and, advantageously, in the form of chlorides thereof.

The catalyst should preferably contain 1 to 60% by weight of said active phase.

In the case of the content of vanadium or titanium chlorides below 1% by weight the catalyst has a low activity, while at the content exceeding 60% by weight, the catalyst activity per unit mass of the transition metal is lowered (i.e. specific activity of the catalyst is reduced).

DETAILED DESCRIPTION OF THE INVENTION

The catalyst is prepared in the following manner.

As the macroporous carriers, in accordance with the present invention, use is made of macroporous copolymers of monovinyl monomers such as sytrene, ethylstyrene, diethylstyrene, isopropylstyrene, methylacrylate, methylmethacrylate with divinyl monomers such as divinylbenzene, ethyldivinylbenzene, diisopropenylbenzene. Such copolymers are produced by radical-type copolymerization in the presence of a pore-forming agent. Specific surface area (m$^2$/g) and total pore volume (cm$^3$/g) of the resulting macroporous copolymers slightly depend on the composition of a monomeric mixture and are defined by the amount and nature of the pore-forming agent.

As the pore-forming agent use is made of low- and high-molecular compounds readily soluble in the monomer mixture, non-copolymerizable and readily-removable from the resulting copolymer.

The amount of the transition metal deposited onto the surface of the polymeric carrier may be varied within any desired range.

To obtain a catalyst based on titanium chloride, the carrier is treated with titanium chloride or a solution thereof in vacuum or in the atmosphere of an inert gas at a temperature within the range of from $-70°$ to $+180°$ C.

It is possible to prepare a catalyst based on titanium chloride by way of treatment of the carrier in succession or in combination with titanium chloride and an organo-aluminum compound (or with solutions thereof) in vacuum or in the atmosphere of an inert gas at a temperature within the range of from $-70°$ to $180°$ C. The resulting catalyst is dried in vacuum at a temperature of $80°$ to $180°$ C.

To prepare a catalyst based on vanadium chloride, the carrier is treated with vapors or solutions of vanadium chloride and dried in vacuum.

A high activity of the catalyst is obtained by using, as the carrier, said macroprous copolymer with a specific surface area within the range of from $30°$ to $700 \, m^2/g$. The use of a carrier with a high specific surface area makes it possible to obtain a catalyst with a finely-dispersed crystalline phase of titanium or vanadium chloride. This brings about a higher efficiency of the compound of the transition metal and an increased activity of the catalyst as well.

The use of macroporous polymeric carriers makes it possible to produce catalysts with a high content of a salt of titanium or vanadium. Macroporosity increases the capacity of the carrier with respect to chlorides of vanadium or titanium.

The use of the carrier according to the present invention enables the production of a highly-active catalyst with the surface of the carrier accessible for the monomer and coated with a salt of the transition metal.

The catalysts according to the present invention are employed in processes of dimerization, oligomerization, and (co)-polymerization of vinyl monomers. These processes occur under high pressure and in vacuum, at concentrations of the monomer of from 0.01 to 100% by weight and at a temperature within the range of from $70°$ to $180°$ C.

Owing to the use of the catalysts, according to the present invention, said processes proceed with a higher yield of dimers, oligomers, and (co)polymers, at a low degree of contamination thereof with inorganic residues which enables the use of said polymeric products without any additional washing.

Another advantage of the present invention is that the granulometric composition of the polymer resulting from the synthesis may be controlled by adjusting the granulometric composition of the catalyst.

The particle size of the polymer depends on the yield of the polymer per unit weight of the catalyst and on particle size of the carrier. The yield of the polymer, in turn, is defined by activity of the catalyst, concentration of the monomer and duration of polymerization.

At equal yields, i.e. under identical polymerization conditions, the polymer particle size is defined by the particle size of the carrier.

For a better understanding of the present invention, some specific Examples illustrating preparation and use of the catalyst are given hereinbelow. In Examples 1 to 27 particle size of the catalyst is determined by the particle size of the carrier.

EXAMPLE 1

Preparation of the catalyst 1.18 g of a carrier with a particle size of from 0.3 to 0.8 mm in the form of spherical granules comprising a copolymer of styrene (70% by weight) with divinylbenzene (30% by weight) with a specific surface area of 160 $m^2/g$ and pore volume of $1.65 \, g/cm^3$ is placed into a dry flask. The flask with the carrier is set under vacuum, the carrier is treated with vapors of titanium chloride in the amount of 0.15 g and cooled. Then it is treated with vapors of diethylaluminum chloride in the amount of 0.065 g. The resulting catalyst is heated to a temperature of $180°$ C. for 3 hours in vacuum. In accordance with the data of analysis, the content of titanium chloride in the thus-prepared catalyst is 1% by weight, that of the carrier is 99% by weight. The catalyst is in the form of spherical granules.

Polymerization of propylene 0.15 g of the catalyst, 1.1 g of diethylaluminum chloride, $5.7 \cdot 10^{-3}$ mole of hydrogen and 130 g of propylene are charged into an autoclave with a stirrer, having a capacity of 300 ml. Polymerization is conducted at the temperature of $60°$ C. under a pressure of 60 atm.g. After 5.5 hours there are obtained 16.9 g of polypropylene with a particle size of 1.5–4 mm in the form of spherical granules. The content of the fraction insoluble in boiling n-heptane is 86% by weight. The yield of the polymer per one gram of titanium is 36.14 kg ash-content is 0.0046% by weight.

EXAMPLE 2

Polymerization of propylene 0.08 g of a catalyst prepared in a manner similar to that described in the foregoing Example 1, with a particle size of from 0.1 to 0.25 mm, 0.76 g of diethylaluminum chloride, $5.7 \times 10^{-3}$ mole of hydrogen and 130 g of propylene are charged into an autoclave with a capacity of 300 ml provided with a stirrer. Polymerization is conducted at a temperature of $60°$ C. under a pressure of 60 atm.g. After 5 hours there are obtained 8 g of polypropylene with a particle size of from 0.5 to 1.4 mm in the form of spherical granules. The yield of the polymer per one gram of titanium is 32 kg, ash-content is 0.0052% by weight. Molecular mass of the thus-prepared polypropylene is $1.5 \times 10^6$.

EXAMPLE 3

Preparation of the Catalyst 5 g of a carrier with a particle size of from 0.5 to 0.9 mm in the form of spherical granules comprising a copolymer of 60% by weight of styrene and 40% by weight of divinyl benzene with a specific surface area of 274 $m^2/g$ and pore volume of 1.56 $cm^3/g$ are placed into a dry flask.

The flask with the carrier is set under vacuum, the carrier is treated with vapors of titanium chloride in the amount of 0.52 g and cooled. Then the carrier is treated with vapors of diethylaluminum chloride in the amount of 0.162 g. The catalyst is heated at a temperature of $180°$ C. for 3 hours in vacuum. Analysis shows that the content of titanium chloride in the resulting catalyst is 1% by weight; the content of the carrier is 99% by weight. The catalyst is in the form of spherical granules.

Polymerization of Propylene 0.1 g of the catalyst, 1 g of diethylaluminium chloride and 130 g of propylene are placed into a 300 ml autoclave. Polymerization of propylene is conducted at a temperature of 70° C. under the pressure of 60 atm.g. After 6.6 hours there are prepared 12.8 g of polypropylene with a particle size of from 2.7 to 5.0 mm in the form of spherical granules. Density of the resulting polymeric particles is 0.87 to 0.92 g/cm$^3$. The yield of polypropylene is 41.1 kg per 1 g of titanium, ash-content is 0.011% by weight.

EXAMPLE 4

Polymerization of Propylene 0.0558 g of the catalyst prepared in Example 3 with a particle size of from 0.25 to 0.5 mm, 0.3093 g of diethylaluminum chloride and 130 g of propylene are placed into a 300 ml autoclave. Polymerization is conducted at a temperature of 70° C. under a pressure of 60 atm.g. After 7 hours there are prepared 7.3 g of polypropylene with a particle size of from 1.5 to 2.8 mm in the form of spherical granules. The yield of polypropylene per one gram of titanium is 41.5 kg, ash-content is equal to 0.0108% by weight.

EXAMPLE 5

Preparation of the Catalyst 0.1412 g of titanium chloride and 0.0599 g of diethylaluminum chloride are mixed in a 100 ml flask under a pressure of $10^{-2}$ mm Hg and at a temperature of $-30°$ C. The resulting mixture is added with 1.08 g of the carrier with a particle size of from 0.03 to 1 mm in the form of spherical granules comprising a copolymer of 60% by weight styrene and 40% by weight of divinylbenzene with a specific surface area of 360 m$^2$/g and pore volume of 1.42 cm$^3$/g.

The flask contents are maintained in vacuum at a temperature of $-10°$ C. The resulting catalyst is maintained at a temperature of 80° C. for 10 hours in vacuum. Analysis shows that the content of titanium chloride in the catalyst is 1% by weight; the content of the carrier is 99% by weight. The catalyst is in the form of spherical granules.

Polymerization of Propylene 0.12 g of the catalyst, 0.3 g of diethylaluminum chloride, $5.7 \times 10^{-3}$ mole of hydrogen and 130 g of propylene are charged into an autoclave with a stirrer. Polymerization is conducted at a temperature of 60° C. under a pressure of 60 atm.g. After 16.5 hours there are produced 27 g of polypropylene with a particle size of from 0.2 to 0.7 mm in the form of spherical granules. The yield of polypropylene is 72.2 kg per 1 g of titanium, ash-content is 0.0023% by weight.

EXAMPLE 6

Preparation of the catalyst 0.3094 g of the carrier with a particle size of from 0.03 to 0.1 mm in the form of spherical granules comprising a copolymer of 85% by weight of styrene and 15% by weight of divinylbenzene with a specific surface area of 97 m$^2$/g and pore volume of 1.25 cm$^3$/g are placed into a flask. The flask with the carrier is set under vacuum and the carrier is successively treated with vapors of titanium chloride in the amount of 0.0687 g and diethylaluminum chloride in the amount of 0.0206 g as described in the foregoing Example 1.

Analysis shows that the catalyst contains 3% by weight of titanium chloride and 97% by weight of the carrier. The catalyst has the form of spherical granules.

Polymerization of Propylene 0.1 g of the catalyst, 0.836 g of diethylaluminum chloride and 130 g of propylene are charged into an autoclave with a capacity of 300 ml provided with a stirrer. Polymerization is conducted at a temperature of 70° C. and under a pressure of 60 atm.g. After 5.9 hours there are prepared 7.8 g of polypropylene in the form of spherical particles with a size of from 0.15 to 0.45 mm. The yield of polypropylene is 8.35 kg per 1 g of titanium, ash-content is 0.029% by weight.

EXAMPLE 7

Preparation of the Catalyst 0.3301 g of the carrier with a particle size of from 0.25 to 0.4 mm in the form of spherical granules comprising a copolymer of 88% by weight of styrene and 12% by weight of diisopropenylbenzene with the specific surface area of 60 m$^2$/g and pore volume of 1.0 cm$^3$/g is treated with a mixture of 0.2545 g of titanium chloride and 0.0824 g diethylaluminum chloride in vacuum as described in the foregoing Example 1. Analysis shows that the catalyst contains 9.82% by weight of titanium chloride and 90.18% by weight of the carrier. The catalyst is in the form of spherical granules.

Polymerization of Propylene 0.17 g of the catalyst, 0.3 g of diethylaluminum chloride and 130 g of propylene are charged into an autoclave with a stirrer. Polymerization is conducted at a temperature of 70° C. under a pressure of 60 atm.g. After 5.85 hours there are prepared 29.5 g of polypropylene with a particle size of from 1.5 to 2.4 mm in the form of spherical granules. The yield of polypropylene is 5.72 kg per one gram of titanium, ash content is 0.08% by weight.

EXAMPLE 8

Polymerization of Ethylene 0.1 g of the catalyst prepared as in the foregoing Example 7 with a particle size of from 0.25 to 0.4 mm, 1 g of diethylaluminum chloride and 110 ml of toluene are placed into the reactor and ethylene is admitted thereinto. Polymerization is conducted at a temperature of 60° C. under a constant pressure of ethylene equal to 0.5 atm.g.

After 8.5 hours there are produced 7 g of polyethylene with a particle size of from 1 to 2.0 mm in the form of spherical granules. The rate of polymerization of ethylene is 530 g of polyethylene/g of titanium.hr.atm.

EXAMPLE 9

Preparation of the Catalyst 0.746 g of the carrier in the form of spherical granules comprising a copolymer of 60% by weight of styrene with 30% by weight of divinylbenzene and 10% by weight of methylmethacrylate with the specific surface area of 134 m$^2$/g and pore volume of 1.34 cm$^3$/g are treated with vapors of titanium chloride in the amount of 0.0971 g and maintained for 5 hours at a temperature of 80° C.

Analysis shows that the catalyst contains 5.6% by weight of titanium chloride, and 94.4% by weight of the carrier. The catalyst is in the form of spherical granules.

Oligomerization of Propylene 0.095 g of the catalyst, 0.94 g of diethylaluminum chloride and 130 g of propylene are charged into an autoclave with a stirrer. Oligomerization is conducted at a temperature of 70° C. under a pressure of 60 atm.g. After 6.4 hours there are produced 11.9 g of liquid oligomers. The yield of oligomers of propylene is 9.1 kg per 1 g of titanium. Molecular mass of the resulting oligomers is about 150.

EXAMPLE 10

Dimerization of Ethylene 0.007 of the catalyst similar to that obtained in Example 9 hereinbefore, 1.08 g of ethylaluminum dichloride and 0.2 l of benzene are charged into an autoclave with a stirrer and ethylene is admitted thereinto. Dimerization is effected at a temperature of 20° C. under a pressure of 25 atm.g. for 2 hours. During the dimerization the pressure of ethylene is maintained constant.

The yield of butenes is 94% by weight. The yield of butenes per one g of titanium is 6,100 kg.

EXAMPLE 11

Preparation of the Catalyst 0.26 g of the carrier with a particle size of from 0.25 to 0.5 mm in the form of spherical granules comprising a copolymer of 60% by weight of styrene and 40% by weight of divinylbenzene with a specific surface area of 260 m$^2$/g and pore volume of 1.5 cm$^3$/g is maintained in vacuum for 4 hours at a temperature of 80° C., cooled to room temperature and treated with vapors of vanadium chloride in the amount of 0.153 g.

Analysis shows that the content of vanadium chloride is 32% by weight, the content of the carrier is 68% by weight. The catalyst is in the form of spherical granules.

Polymerization of Propylene 0.045 g of the catalyst, 0.04 g of Al(i-C$_4$H$_9$)$_3$ and 50 ml of n-heptane are charged into a reactor with a stirrer. At a temperature of 60° C. propylene is admitted into the reactor and polymerization is conducted under a constant pressure of propylene of 470 mm Hg.

Within 2 hours there is obtained 1.32 g of polypropylene with a particle size of 2–3 mm in the form of spherical granules. The polymerization rate is 240 g/g titanium hr.atm.

The content of the fraction insoluble in n-heptane is 83% by weight. The density of particles is as high as 0.9 g/cm$^3$. Molecular mass of the polymer is about 10$^6$.

EXAMPLE 12

Polymerization of Propylene 0.067 g of a catalyst similar to that produced in Example 11 hereinbefore with a particle size of from 0.001 to 0.03 mm, 0.06 g of triisobutylaluminum and 70 ml of n-heptane are charged into a reactor with a stirrer. At a temperature of 60° C. propylene is admitted thereinto and polymerization is conducted under a constant pressure of the monomer of 470 mm Hg. After 2 hours there are produced 2.4 g of polypropylene in the form of a powder with a particle size of from 0.2 to 0.4 mm.

The yield of polypropylene is 0.334 kg per one gram of vanadium. Polymerization rate is 270 g/g of vanadium.hr.atm.

EXAMPLE 13

Preparation of the Catalyst 0.187 g of the carrier with a particle size of from 0.25 to 0.5 mm in the form of spherical granules comprising a copolymer of 60% by weight of styrene and 40% by weight of divinylbenzene with a specific surface area of 260 m$^2$/g and pore volume of 1.5 cm$^3$/g is prepared as described in Example 11 hereinabove and treated with vapors of vanadium chloride in the amount of 0.35 g.

The resulting catalyst is dried under vacuum at a temperature of 80° C.

The analysis shows that the content of vanadium chloride is 60% by weight, the content of the carrier is 40% by weight. The catalyst is in the form of spherical granules.

Polymerization of Propylene 0.0873 g of the catalyst, 0.0927 g of Al(i-C$_4$H$_9$)$_3$ and 70 ml of n-heptane are charged into a reactor with a stirrer. At the temperature of 60° C. propylene is admitted thereinto and polymerization is performed under a constant pressure of the monomer of 470 mm Hg.

After two hours there are prepared 3.7 g of the polymer with a particle size of 2–3 mm in a form of spherical granules. The yield of polypropylene is 0.216 kg per one gram of vanadium. The polymerization rate is 175 g/g vanadium hr.atm.

EXAMPLE 14

Polymerization of Ethylene 0.046 g of a catalyst similar to that produced in the foregoing Example 11 with a particle size of from 0.001 to 0.03 mm, 0.025 g of triisobutylaluminum and 50 ml of n-heptane are charged into a reactor with a stirrer. At a temperature of 80° C. ethylene is admitted thereinto and polymerization is carried out under a constant pressure of a monomer of 223 mm Hg.

After 3 hours there are produced 11.1 g of polyethylene in the form of a powder with a particle size of from 0.2 to 0.5 mm.

The yield of polyethylene is 2.38 kg per 1 g of vanadium. The polymerization rate is equal to 2,700 g/g vanadium.hr.atm.

EXAMPLE 15

Preparation of the Catalyst 0.903 g of the carrier with a particle size of from 0.25 to 0.5 mm in the form of spherical granules comprising a copolymer of 60% by weight of styrene and 40% by weight of divinylbenzene with a specific surface area of 260 m$^2$/g and pore volume of 1.5 cm$^3$/g is prepared as described in Example 11 hereinbefore and treated with vapors of vanadium chloride in the amount of 1.01 g.

The resulting catalyst is set under vacuum at a temperature of 80° C. Analysis shows that the content of vanadium chloride is 47% by weight, the content of the carrier is 53% by weight. The catalyst is in the form of spherical granules.

Polymerization of Ethylene 0.047 g of a catalyst with a particle size of from 0.25 to 0.5 mm, 0.036 g of Al(i-C$_4$H$_9$)$_3$, 50 ml of n-heptane are charged into a reactor with a stirrer. Ethylene is admitted thereinto at a temperature of 80° C. and polymerization is conducted under constant pressure of the monomer of 223 mm Hg. After 6 hours there are produced 0.082 g of polyethylene with a particle size of from 0.75 to 2 mm in the form of spherical granules. The yield of the polymer is 0.012 kg per one gram of vanadium. The polymerization rate is 6.6 g/g vanadium.hr.atm.

EXAMPLE 16

Polymerization of Butene 0.02 g of the catalyst prepared as in Example 15 hereinabove with a particle size of from 0.25 to 0.5 mm, 0.042 g of triisobutylaluminum and 17 ml of n-heptane are charged into a dilatometer provided with a stirrer and 0.47 g of a liquid α-butene is added thereto. The dilatometer is placed into a thermostat at a temperature of 50° C. After 4 hours there is obtained 0.45 g of poly-α-butene with a particle size of from 1.5 to 2 mm in the form of spherical granules. The polymer yield is 0.45 kg per one gram of vanadium. The polymerization rate is equal to 42 g/g vandium hr.atm.

EXAMPLE 17

Polymerization of Ethylene 0.0188 g of the catalyst prepared in the foregoing Example 11 with a particle size of from 0.001 to 0.03 mm, 0.011 g of triisobutylaluminum and 300 ml of n-heptane are charged into a reactor with a stirrer. At a temperature of 80° C. ethylene is admitted thereinto and polymerization is conducted under a constant pressure of ethylene of 223 mm Hg. After 25 hours there are produced 39 g of polyethylene. The polymer yield is 20.4 kg per 1 g of vanadium. The polymerization rate is 2,780 g/g vanadium hr.atm.

EXAMPLE 18

Polymerization of 4-Methylpentene-1

0.05 g of the catalyst produced in Example 5 hereinbefore is charged into a dry ampule, added with 0.7 g of (C$_2$H$_5$)$_2$AlCl and 12.5 g of 4-methylpentene-1. The ampule is sealed and placed into a thermostat with a temperature of 50° C. After 3.5 hours there is produced 0.2 g of poly-4-methylpentene-1.

The polymer yield is 1.28 kg per gram of titanium.

EXAMPLE 19

Copolymerization of Ethylene and Propylene 0.15 g of the catalyst prepared in Example 5 hereinbefore 0.5 g of (i-C$_4$H$_9$)$_2$AlCl and 50 ml of n-heptane are charged into an apparatus with a stirrer. A mixture of ethylene with propylene is admitted into a reactor at the temperature of 70° C. After 4 hours methanol is added thereto. The precipitated copolymer is separated, dried and weighed. The yield of the copolymer of ethylene and propylene is 2.12 kg per one gram of titanium.

EXAMPLE 20

Preparation of the Catalyst 12.11 g of a carrier in the form of spherical granules comprising a copolymer of 60% by weight of styrene and 40% by weight of divinylbenzene with a specific surface area of 360 m$^2$/g and pore volume of 1.42 cm$^3$/g are treated with vapors of titanium chloride in a manner similar to that described in Example 9 hereinbefore. The content of titanium chloride in the resulting catalyst is 48.5% by weight; the catalyst is in the form of spherical granules.

Dimerization of Ethylene 0.0967 g of the catalyst, 0.417 g of (C$_2$H$_5$)$_2$AlCl and 0.2 liters of benzene are placed into an autoclave provided with a stirrer. Dimerization is effected at a temperature of 80° C. under a constant pressure of ethylene of 25 atm.g. After 2 hours methanol is added into the reaction mixture. The resulting products are isolated and identified. The yield of ethylene dimers is 32 g, whereform 97% by weight is butene-1, 3% by weight is cis-butene-2.

EXAMPLE 21

Preparation of the Catalyst 1.08 g of a carrier in the form of spherical granules, comprising a copolymer of 50% by weight of styrene, 20% by weight of methylmethacrylate and 30% by weight of divinylbenzene with a specific surface area of 197 m$^2$/g and pore volume of 0.8 cm$^3$/g, are treated with vapors of titanium chloride in the amount of 0.14 g and (C$_2$H$_5$)$_2$AlCl in the amount of 0.06 g in a manner similar to that described in Example 1.

The resulting catalyst contains 2.5% by weight of titanium chloride and is in the form of spherical granules.

Dimerization of Ethylene 0.116 g of the catalyst, 0.417 g of (C$_2$H$_5$)AlCl$_2$ and 0.2 liters of benzene are charged into an autoclave provided with a stirrer. Dimerization is effected at a temperature of 20° C. under a pressure of ethylene of 25 atm.g. for 2 hours.

The yield of butene-1 is equal to 19 g which corresponds to 40% conversion of ethylene.

EXAMPLE 22

Preparation of the Catalyst

The catalyst is prepared following the procedure similar to that of Example 9 hereinbefore. As the carrier use is made of a copolymer of 70% by weight of styrene with 30% by weight of methylmethacrylate with a specific surface area of 30 m$^2$/g and pore volume of 0.9 cm$^3$/g in the form of irregularly-shaped granules. The content of titanium chloride is 5.6% by weight. The catalyst is also in the form of irregularly-shaped granules.

Dimerization of Ethylene

Dimerization is effected following the procedure of Example 20 hereinbefore. After 2 hours there are produced 9.8 g of polyethylene and 533 g of butenes of the following composition: 63.8% by weight of butene-1; 21.7% by weight of cis-butene-2; 14.5% by weight of trans-butene-2. The yield of butenes per one gram of titanium is 300 kg.

EXAMPLE 23

Preparation of the Catalyst 7.4 g of a carrier in the form of irregularly-shaped granules comprising a copolymer of 40% by weight of styrene, with 60% by weight of divinylbenzene with a specific surface area of 360 m²/g and pore volume of 1.42 cm³/g are placed into a flask and treated with 6 g of $(C_2H_5)_2AlCl$. 0.4 g of the thus-treated carried are mixed with 0.8 g of the catalyst prepared as in Example 9 hereinbefore. The mixture is kept for 2 days at room temperature and then dried under vacuum of $2.10^{-2}$ mm Hg.

THe content of titanium chloride in the resulting catalyst is 38.7% by weight. The catalyst is in the form of irregularly-shaped granules.

Oligomerization of Propylene 0.75 g of the catalyst, 1.4 g of $(C_2H_5)_2AlCl$ and 400 g of propylene are charged into an autoclave provided with a stirrer. The process is conducted at the temperature of 70° C. After 4 hours there are produced 14 g of oligomers of propylene.

EXAMPLE 24

Preparation of the Catalyst 4 g of a carrier with a particle size of from 0.2 to 0.7 mm in the form of spherical granules and comprising a copolymer of 50% by weight of styrene, 20% by weight of 4-vinylpyridine and 30% by weight of commercial divinylbenzene with a specific surface area of 176 m²/g and pore volume of 1.2 cm³/g are treated with 0.8 g of titanium chloride and 25 g of $(C_2H_5)_2AlCl$ in a manner similar to that described in Example 1.

The content of titanium chloride in the thus-prepared catalyst is 6% by weight. The catalyst is in the form of spherical granules.

Polymerization of Propylene 0.4 g of the catalyst, 0.2 g of triethylaluminum and 130 g of propylene are charged into an autoclave provided with a stirrer. The process is conducted at a temperature of 70° C. for two hours. The yield of polypropylene is 33 g; its particle size is 1–4 mm; the product is in the form of spherical granules.

EXAMPLE 25

Preparation of the Catalyst 3.5 g of a carrier with a particle size of from 0.035 to 0.08 mm in the form of spherical granules, comprising a copolymer of 70% by weight of styrene and 30% by weight of divinylbenzene with a specific surface area of 700 m²/g and pore volume of 0.3 cm³/g are treated with 0.37 g of titanium chloride and 0.15 g of diethylalumum chloride in a manner similar to that of Example 1. The resulting catalyst contains 7% by weight of titanium chloride and is in the form of spherical granules with a size of from 0.035 to 0.08 mm.

Oligomerization of Propylene 0.14 g of the catalyst, 0.21 g of diethylaluminum chloride and 130 g of propylene are charged into an autoclave provided with a stirrer. Oligomerization is conducted at a temperature of 70° C. for two hours. The yield of liquid oligomers of propylene is 5 g.

EXAMPLE 26

Preparation of the Catalyst 0.26 g of a carrier in the form of spherical granules, comprising a copolymer of 70% by weight of styrene and 30% by weight of divinylbenzene with a specific surface area of 260 m²/g and pore volume of 1.5 cm³/g are kept in vacuum for 4 hours at a temperature of 80° C., cooled to room temperature and treated with vapors of vanadium chloride. The resulting catalyst is set under vacuum of $10^{-3}$ mm Hg at a temperature of 80° C. The content of vanadium chloride in the thus-prepared catalyst is 31.1% by weight. The catalyst is in the form of spherical granules.

Polymerization of Alpha-butene 0.02 g of the catalyst, 0.042 g of triisobutylaluminum, 17 ml of n-heptane and 0.47 g of liquid alpha-butene are charged into a dilatometer provided with a stirrer. The dilatometer is placed into a thermostat with a temperature of 50° C. After a 4-hours' polymerization there is obtained 0.45 g of poly-α-butene which corresponds to 225 g per gram of vanadium.

EXAMPLE 27

Preparation of the Catalyst

The catalyst is prepared in a manner similar to that of Example 26 hereinabove. As the carrier use is made of a copolymer of 40% by weight of styrene and 60% by weight of divinylbenzene with a specific surface area of 500 m²/g and pore volume of 2.8 cm³/g in the form of spherically-shaped particles with a size of from 0.035 to 0.08 mm. The content of vanadium chloride in the thus-prepared catalyst is 10% by weight. The catalyst is in the form of spherical granules.

Polymerization of Propylene 0.303 g of the catalyst, 0.05 g of isobutylaluminium, 50 ml of n-heptane are charged into a reactor provided with a stirrer. Propylene is admitted thereinto at a temperature of 60° C. and polymerization is carried out under a constant pressure of propylene of 470 mm Hg. The polymerization time is 6 hours. The yield of polypropylene is 1.46 g; the product has the form of spherically-shaped granules with a size of from 0.15 to 0.35 mm. The propylene polymerization rate is equal to 40 g per g of vanadium.hr.atm.

What is claimed is:

1. In a catalyst for di-, oligo-, co- and poly- merization of the vinyl monomers comprising an active phase, which consists of a transition metal compound selected from Groups IV-V of the periodic system and a cocatalyst consisting of an organo-aluminum compound, the improvement of which comprises depositing said catalyst onto a polymeric carrier comprising a macroporous copolymer of vinyl and divinyl monomers with a specific surface area of from 30 to 700 m²/g.

2. A catalyst as claimed in claim 1, wherein said carrier has a pore volume of from 0.3 to 2.8 cm³/g.

3. A catalyst as claimed in claim 1, wherein the carrier is made of a copolymer of styrene and divinylbenzene.

4. A catalyst as claimed in claim 1, wherein the carrier is made of a copolymer of styrene and diisopropenylbenzene.

5. A catalyst as claimed in claim 1, wherein the carrier is made of a copolymer of styrene, divinylbenzene and methylmethacrylate.

6. A catalyst as claimed in claim 1, wherein the carrier is made of a copolymer of styrene, ethyldivinylbenzene and vinylpyridine.

7. A catalyst as claimed in claim 1, having a particle size of from 0.001 to 1 mm.

8. A catalyst as claimed in claim 1, having a granulated form.

9. A catalyst as claimed in claim 1, wherein the active phase is made of a compound of a metal selected from the group consisting of vanadium and titanium.

10. A catalyst as claimed in claim 1, wherein the content of the active phase ranges from 1 to 60% by weight.

11. A catalyst as claimed in claim 9, wherein the active phase is titanium chloride.

12. A catalyst as claimed i claim 9, wherein the active phase is vanadium chloride.

* * * * *